(12) United States Patent
Tuszynski et al.

(10) Patent No.: US 7,157,435 B2
(45) Date of Patent: Jan. 2, 2007

(54) METHODS FOR MODULATION OF THE EFFECTS OF AGING ON THE PRIMATE BRAIN

(75) Inventors: Mark H. Tuszynski, La Jolla, CA (US); Armin Blesch, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 353 days.

(21) Appl. No.: 09/730,790

(22) Filed: Dec. 5, 2000

(65) Prior Publication Data

US 2001/0043920 A1  Nov. 22, 2001

Related U.S. Application Data

(63) Continuation-in-part of application No. 09/620,174, filed on Jul. 19, 2000, now Pat. No. 6,683,058, which is a continuation-in-part of application No. 09/060,543, filed on Apr. 15, 1998, now Pat. No. 6,451,306.

(51) Int. Cl.
| | |
|---|---|
| *A01N 43/04* | (2006.01) |
| *A01N 63/00* | (2006.01) |
| *C12N 15/00* | (2006.01) |
| *C12N 15/63* | (2006.01) |
| *C07H 21/04* | (2006.01) |

(52) U.S. Cl. ............... 514/44; 435/320.1; 435/455; 424/93.2; 424/93.21; 536/23.5

(58) Field of Classification Search ............ 514/44; 435/320.1, 325, 455; 536/23.5; 424/93.21, 424/93.2
See application file for complete search history.

(56) References Cited

U.S. PATENT DOCUMENTS

| | | | |
|---|---|---|---|
| 5,082,670 A | 1/1992 | Gage et al. | |
| 5,529,774 A | 6/1996 | Barba et al. | |
| 5,580,859 A * | 12/1996 | Felgner et al. | 514/44 |
| 5,650,148 A | 7/1997 | Gage et al. | |
| 5,683,695 A | 11/1997 | Shen et al. | |
| 5,756,312 A | 5/1998 | Weiner et al. | |
| 5,762,926 A | 6/1998 | Gage et al. | |
| 6,451,306 B1 | 9/2002 | Tuszynski et al. | |
| 6,683,058 B1 | 1/2004 | Tuszynski | |

FOREIGN PATENT DOCUMENTS

WO    WO 90/06757    6/1990

OTHER PUBLICATIONS

Deonarain, 1998, Expert Opin. Ther. Pat., vol. 8, pp. 53-69.*
Verma et al., 1997, Nature, vol. 389, pp. 239-242.*
Eck et al., 1996, Goodman & Gilman's The Pharmacological Basis of Therapeutics, McGraw-Hill, New York, p. 77-101.*
Gorecki, 2001, Expert Opin. Emerging Drugs, 6(2): 187-198.*
Castro et al., 2001, Histl. Histopathol., vol. 16, p. 1225-1238.*
Mandel et al., 1999, Experimental Neurology, vol. 155, No. 1, pp. 59-64.*
Kojima, et al., "Adenovirus-Mediated transduction with human glial cell line-derived neurotrophic factor gene prevents 1-methyl-4-phenyl-1,2,3,6-tetrahydropyridine-induced dopamine depletion in striatum of mouse brain," *Biochemical and Biophysical Research Communications*, 238:569-573 (1997).
Roberts, et al., "Effects of NGF-Secreting Genetically Modified Cell Grafts on Cholinergic Neuronal Morphology and Gocnition in Aged Primates," *Soc. For Neuroscience Abstracts*, 21(2):613.8 (1995).
Yang, et al., "Gene Therapy for Central Nervous System Injury: The Use of Cationic Liposomes: An Invited Review," *Journal of Neurotrauma*, 14(5):281-297 (1997).
Zlokovic, et al., "Cellular and Molecular Neurosurgery: Pathways From Concept to Reality—Part II: Vector Systems and Delivery Methodologies for Gene Therapy of The Central Nervous System," *Neurosurgery*, 40(4):805-813 (1997).
Armelin et al., "Pituitary extracts and steroid hormones in the control of 3T3 cell growth" *Proc. Natl. Acad. Sci.* (1973) 70:2702-6.
Banerji et al., "Expression of a beta-globin gene is enhanced by remote SV40 DNA sequences" *Cell* (1981) 27:299-308.
Benoist et al., "In vivo sequence requirements of the SV40 early promoter region" *Nature* (1981) 290:304-10.
Blesch et al., "Ex vivo gene therapy for Alzheimer's disease and spinal cord injury" *Clinical Neuroscience* (1996) 3:268-274.
Borsani et al., "cDNA sequence of human beta-NGF" *Nucleic Acids Res.* (1990) 18:4020.
Breathnach et al., "Organization and expression of eucaryotic split genes coding for proteins" *Ann. Rev. Biochem.* (1981) 50:349-83.

(Continued)

*Primary Examiner*—Shin-Lin Chen
(74) *Attorney, Agent, or Firm*—Foley & Lardner LLP

(57) ABSTRACT

The invention provides a clinically useful protocol for delivery of recombinant nervous system growth factors into the aging mammalian brain. The invention is particularly useful in tempering and reversing the loss of neurological function in the aging mammalian brain, by (a) correlating loss of cortical fiber density to impairment of neurological function in the normal, aging brain; and (b) providing minimally invasive means by which such losses may be reversed. To these ends, a method is provided by which a growth factor-encoding transgene is delivered to, and expressed in, preselected sites within the brain, to stimulate growth of neurons at, and at a distance from, each delivery site.

21 Claims, 2 Drawing Sheets

OTHER PUBLICATIONS

Chen et al., "Calcium phosphate-mediated gene transfer: a highly efficient transfection system for stably transforming cells with plasmid DNA" *BioTechniques* (1988) 6:632-8.

Chen et al., "High-efficiency transformation of mammalian cells by plasmid DNA" *Mol. Cell. Biol.* (1987) 7:2745-52.

Chua et al., "Tumor necrosis factor-alpha induces mRNA for collagenase and TIMP in human skin fibroblasts" *Connect. Tissue Res.* (1990) 25:161-170.

Conner et al., "Distribution of NGF delivered into the rat CNS by either grafted NGF-secreting fibroblasts, intraparenchymal (IP) injections, or IP-infusions" *Society for Neuroscience* (1997) 23:53 Abstract 29.5.

Corden et al., "Promoter sequences of eukaryotic protein-coding genes." *Science* (1980) 209:1406-14.

DePamphilis et al., "Microinjecting DNA into mouse ova to study DNA replication and gene expression and to produce transgenic animals" *BioTechniques* (1988) 6:662-80.

de Wet et al., "The mRNAs for the pro-alpha 1(I) and pro-alpha 2(I) chains of type I procollagen are translated at the same rate in normal human fibroblasts and in fibroblasts from two variants of osteogenesis imperfecta with altered steady state ratios of the two mRNAs" *J. Biol. Chem.* (1983) 258:14385-9.

Elias et al., "Regulation of human lung fibroblast collagen production by recombinant interleukin-1, tumor necrosis factor, and interferon-gamma" *Ann. N.Y. Acad. Sci.* (1990) 580:233-244.

Felgner et al., "Cationic liposome mediated transfection" *Proc. West. Pharmacol. Soc.* (1989) 32:115-21.

Felgner et al., "Cationic liposome mediated transfection" *Focus.* (1989) 11:21-25.

Felgner et al., "Lipofection: a highly efficient, lipid-mediated DNA-transfection procedure" *Proc. Natl. Acad. Sci.* (1987) 84:7413-7.

Fraley et al., "New generation liposomes: the engineering of an efficient vehicle for intracellular delivery of nucleic acids" *Trends Biochem. Sci.* (1981) 6:77-80.

Fromm et al., "Deletion mapping of DNA regions required SV40 early region promoter function in vivo" *J. Mol. Appl. Genet.* (1982) 1:457-81.

Gruss et al., "Simian virus 40 tandem repeated sequences as an element of the early promoter" *Proc. Natl. Acad. Sci.* (1981) 78:943-7.

Hefti et al., "Nerve growth factor and Alzheimer's disease" *Ann. Neurol.* (1986) 20:275-81.

Higgins et al., "NGF receptor gene expression is decreased in the nucleus basalis in Alzheimer's disease" *Exp. Neurol.* (1989) 106:222-36.

Horellou et al., "Adenovirus-mediated gene transfer to the central nervous system for Parkinson's Disease" *Experimental Neurobiology* (1997) 144:131-8.

Jolly et al., "Elements in the long terminal repeat of murine retroviruses enhance stable transformation by thymidine kinase gene" *Nucleic Acids Res.* (1983) 11:1855-1872.

Kobayashi et al., "Morphometric study on the CH$ of the nucleus basalis of Meynert in Alzheimer's disease" *Mol. Chem. Neuropathol.* (1991) 15:193-206.

Kordower et al., "The aged monkey basal forebrain: Rescue and sprouting of axotomized basal forebrain neurons after grafts of encapsulated cells secreting human nerve growth factor" *Proc. Natl. Acad. Sci.* (1994) 91:10898-10902.

Lehericy et al., "Heterogeneity and selectivity of the degeneration of cholinergic neurons in the basal forebrain of patients with Alzheimer's disease" *J. Comp. Neurol.* (1993) 330:15-31.

Levivier et al., "Intrastriatal implantation of fibroblasts genetically engineered to produce brain-derived neurotrophic factor prevents degeneration of dopaminergic neurons in a rat model of Parkinson's disease" *The Jo. Of Neuroscience* (1995) 15:7810-20.

Mannino et al., "Liposome mediated gene transfer" *Biotechniques* (1988) 6:682-90.

Maxam et al., "Sequencing end-labeled DNA with base-specific chemical cleavages" *Methods in Enzymology* (1980) 65:499-560.

McCutchan et al., "Enhancement of the infectivity of simian virus 40 deoxy ribonucleic acid with diethylaminoethyl-dextran" *J. Natl. Cancer Inst.* (1968) 41:351-7.

Messing et al., "A system for shotgun DNA sequencing" *Nucleic Acids Res.* (1981) 9:309-21.

Mesulam et al., "Cholinergic innervation of cortex by the basal forebrain: cytochemistry and cortical connections of the septal area, diagonal band nuclei, nucleus basalis (substantia innominata), and hypothalamus in the rhesus monkey." *J. Comp. Neurol.* (1983) 214:170-197.

Moreau et al., "The SV40 72 base repair repeat has a striking effect on gene expression both in SV40 and other chimeric recombinants" *Nucleic Acids Res.* (1981) 9:6047-6068.

Mufson et al., "Loss of nerve growth factor receptor-containing neurons in Alzheimer's disease: A quantitative analysis across subregions of the basal forebrain" *Exp. Neurol.* (1989) 105:221-32.

Mufson et al., "Nerve growth factor receptor expressing human basal forebrain neurons: pathologic alterations in Alzheimer's and Parkinson's disease" *Prog. Clin. Biol. Res.* (1989) 317:401-14.

Palmer et al., "Genetically modified skin fibroblasts persist long after transplantation but gradually inactivate introduced genes" *Proc. Natl. Acad. Sci.* (1991) 88:1330-4.

Potter et al., "Electroporation in biology: methods, applications, and instrumentation" *Anal. Biochem.* (1988) 174:361-73.

Prockop et al., "Heritable diseases of collagen" *N. Eng. J. Med.* (1984) 311:376-86.

Raymon et al., "Application of ex vivo gene therapy in the treatment of Parkinson's disease" *Experimental Neurobiology* (1997) 144:82-91.

Rossi et al., "Identification of a cell-specific transcriptional enhancer in the first intron of the mouse alpha 2 (type I) collagen gene" *Proc. Natl. Acad. Sci.* (1987) 84:5590-4.

Schmidt et al., "Regulation of a collagen promoter by the product of viral mos oncogene" *Nature* (1985) 314:286-9.

Seliger et al., "Gamma interferon regulates long terminal repeat-controlled oncogene expression in transformed mouse fibroblasts at the level of mRNA transcription" *J. Virology* (1988) 62:619-21.

Seliger et al., "Tumor necrosis factor-alpha affects LTR-controlled oncogene expression in transformed mouse fibroblasts at the post-transcriptional level" *J. Immunol.* (1988) 141:2138-44.

Shivaloff et al., "Lines of therapeutic research in Alzheimer's disease" *Psychopharmacology Bulletin* (1996) 32:343-52.

Smith et al., "Age-associated neuronal atrophy occurs in the primate brain and is reversible by growth factor gene therapy" *Proc. Natl. Acad. Sci.* (1999) 96:10893-8.

Smith et al., "Characterization of collagen synthesized by normal and chemically transformed rat liver epithelial cell lines" *Biochem.* (1980) 19:1820-5.

Toneguzzo et al., "Electric field-mediated DNA transfer: transient and stable gene expression in human and mouse lymphoid cells" *Molec. Cell. Biol.* (1986) 6:703-6.

Tuszynski et al., "Gene therapy in the adult primate brain: intraparenchymal grafts of cells genetically modified to produce nerve growth factor prevent cholinergic neuronal degeneration" *Gene Therapy* (1996) 3:305-14.

Tuszynski et al., "Recombinant human nerve growth factor infusions prevent cholinergic neuronal degeneration in the adult primate brain" *Ann.. Neurol.* (1991) 30:325-36.

Tuszynski et al., "Somatic gene therapy for nervous system disease" *Ciba Foundation Symposium 196, Growth factors as drugs for neurological and sensory disorders* (1996) 196:85-97.

Tuszynski et al., "The chronically injured spinal cord exhibits responsiveness to NGF delivered locally by gene therapy" *Society for Neuroscience* (1995) 21:1562 Abstract 613.3.

Ullrich et al., "Human beta-nerve growth factor gene sequence highly homologous to that of a mouse" *Nature* (1983) 303:821-5.

Wolff et al., "Expression of retrovirally transduced genes in primary cultures of rat hepatocytes" *Proc. Natl. Acad. Sci.* (1987) 84:3344-8.

Schinstine et al. (1995) Polymer-encapsulated Schwannoma cells expressing human nerve growth factor promote the survival of cholinergic neurons after a fimbria-fornix transaction. Cell Transplantation; 4:93-102.

Martinez-Serrano et .al. (1995) CNS-Derived Neural Progenitor Cells for Gene Transfer of Nerve Growth Factor to the Adult Rat Brain: Complete Rescue of Axotomized Cholinergic Neurons after Transplantation into the Septum. The J. of Neuroscience, 15(8): 5668-5680.

Rogawski MA (2004) What is the Rational for New Treatment Strategies in Alzheimer's Disease? CNS Spectrums. 9:6-12.

Counts et al. Reduction of Cortical TrkA but Not p75NTR protein in Early-Stage Alzheimer's Disease. American Neurological Association: 56:520-531.

Orkin et al., Report and Recommendations of the Panel to assess the NIH investment in Research on Gene Therapy (Dec. 7, 1995) 1-41.

Marshall. Gene Therapy's Growing Pains (1995) Science 269:1050-1055.

Reichardt et al. (2004) Going the distance, or not with neurotrophin signals. Cell. 118-141-143.

Tuszynski, et al., Nat.Medicine, 11:551-555, 2005.

Mahoney and Saltzmann, J.Pharm.Sci., 85:1276-1281, 1996.

Mahoney and Saltzman, PNAS USA, 8:4536-4539, 1999.

Fung, et al., Cancer Res., 58:672-684, 1998.

Kotulak, Chicago Tribune, Aug. 16, 2005, "Re-engineering the Diseased Brain" (as reprinted online at www.charlotte.com).

* cited by examiner

METHODS FOR MODULATION OF THE EFFECTS OF AGING ON THE PRIMATE BRAIN

RELATED U.S. PATENT APPLICATIONS

This is a continuation-in-part of, and claims the priority of, U.S. patent application Ser. No. 09/620,174, which was filed on Jul. 19, 2000, now U.S. Pat. No. 6,683,058, which is in turn a continuation-in-part of U.S. patent application Ser. No. 09/060,543, which was filed on Apr. 15, 1998, now U.S. Pat. No. 6,451,306.

FIELD OF THE INVENTION

The invention relates to methods for treatment of neurodegenerative disease and methods for delivery of neurotrophic factors into the mammalian brain.

HISTORY OF THE RELATED ART

Neurotrophic factors play a physiological role in the development and regulation of neurons in mammals. In adults, basal forebrain cholinergic neurons, motor neurons and sensory neurons of the CNS retain responsiveness to neurotrophic factors and can regenerate after loss or damage in their presence. For this reason, growth factors are considered to have great promise as drugs for the treatment of neurodegenerative conditions such as Alzheimer's Disease (AD), Parkinson's Disease (PD), amyotrophic lateral sclerosis (ALS), peripheral sensory neuropathies and spinal cord injuries.

In contrast, degenerative changes in the brain due to the normal process of aging have not been well defined in primates. Although prior studies have reported age-related declines in some transmitter systems in the cortex (Emborg, M. E., et al, (1998) Journal of Comparative Neurology 401, 253–65; Fischer, W., et al., (1992) Neurobiology of Aging 13, 9–23; Luine, V., and Hearns, M. (1990) Brain Research 523, 321–4; Fischer, W., et al., (1989), Eur. J. Neurosci. 1, 34–45; Gallagher, M., et al., (1990) Neurobiology of Aging 11, 507–14; Siddiqi, Z., et al., (1999) Journal of Neuropathology and Experimental Neurology 58, 959–71; Siddiqi, Z. A., and Peters, A. (1999) Journal of Neuropathology and Experimental Neurology 58, 903–20; Wenk, et al, (1989) Neurobiology of Aging 10, 11–9), structural alterations in neocortical systems have not been previously described. Thus, little attention has been paid to the possibility that exogenous growth factor delivery could modulate the process of normal aging in the primate brain.

SUMMARY OF THE INVENTION

The invention provides a clinically useful protocol for delivery of recombinant nervous system growth factors into the aging mammalian brain. The invention is particularly useful in tempering and reversing the loss of neurological function in the aging mammalian brain, by (a) correlating loss of cortical fiber density to impairment of neurological function in the normal, aging brain; and (b) providing means by which such losses may be reversed.

More specifically, the invention consists of methods for intraparenchymal delivery of a recombinant growth factor or other growth-promoting gene growth factor(generically, molecules which act on neuronal tissue to stimulate axonal growth) to the mammalian brain. Delivery of the growth factors to targeted cells is achieved by in vivo transduction of neurons targeted for treatment, by transfection of cells neighboring these target neurons (neurons or glia) with a recombinant expression vector for expression of the desired growth factor in situ, and/or by ex vivo grafting of transgene expressing host cells to targeted tissue.

Growth factors delivered according to the invention exert a trophic effect at or near the delivery site (along chemotropic gradients stemming from the delivery site). Startlingly, such growth factors also exert non-chemotropic effects on distant axonal termini. Thus, the invention provides an opportunity to improve neuronal function over relatively expansive sectors of the brain while minimizing surgical invasion into brain tissue.

Control-aged monkeys (red bars) exhibit a significant decline in cortical cholinergic innervation compared to young intact animals (black bars) in most cortical regions. Aged recipients of NGF-secreting grafts (blue bars) exhibit a significant reversal of age-related loss in cholinergic innervation; however, this effect is significant only in cortical regions (insula and inferior temporal cortex) innervated primarily by cholinergic neurons of the intermediate division of Ch4, which was targeted for grafting. Numbers in parentheses below each cortical region indicate p value for ANOVA.

Figure 1:
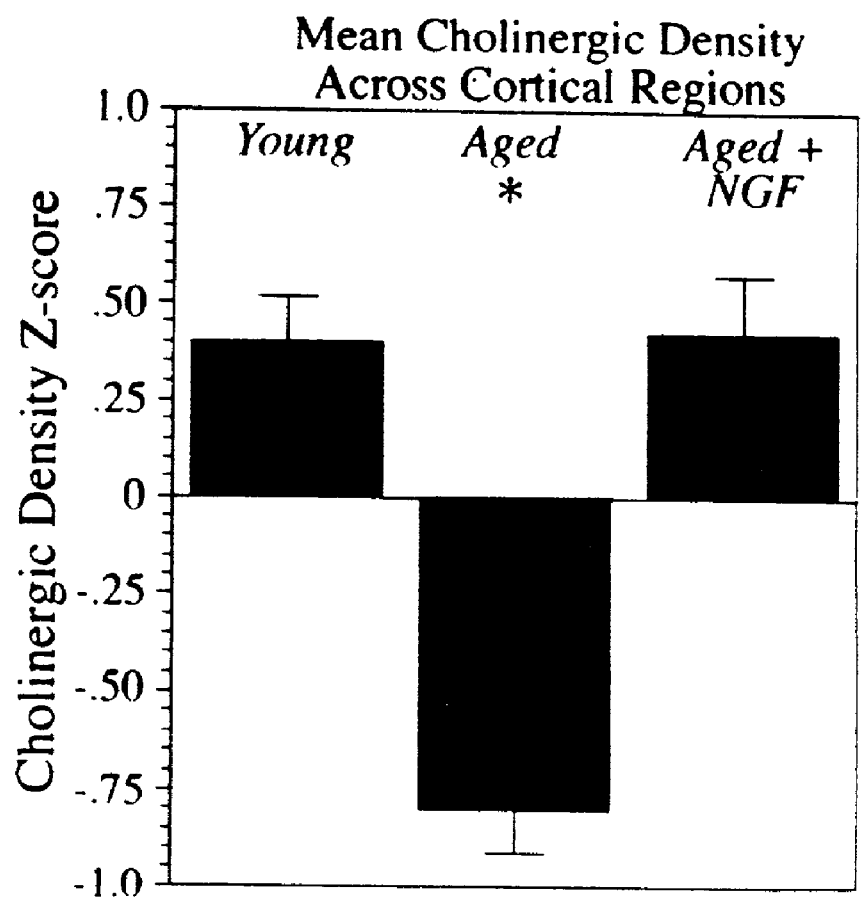
FIG. 1: Quantification of cholinergic axon density. To compare cholinergic innervation densities across multiple cortical regions, normalized z-scores of density measurements from each cortical region were calculated and then averaged. A significant overall group effect was present by one way ANOVA ($p<0.0001$). Aging was associated with a significant reduction in overall cholinergic fiber density (* $p<0.0001$, Post hoc Fischer's), and this was restored in recipients of NGF-secreting cells. Black bars, young monkeys; red bars, aged-controls; blue bars, aged-NGF-grafted subjects. Error bars represent standard errors of the mean.
Figure 2:
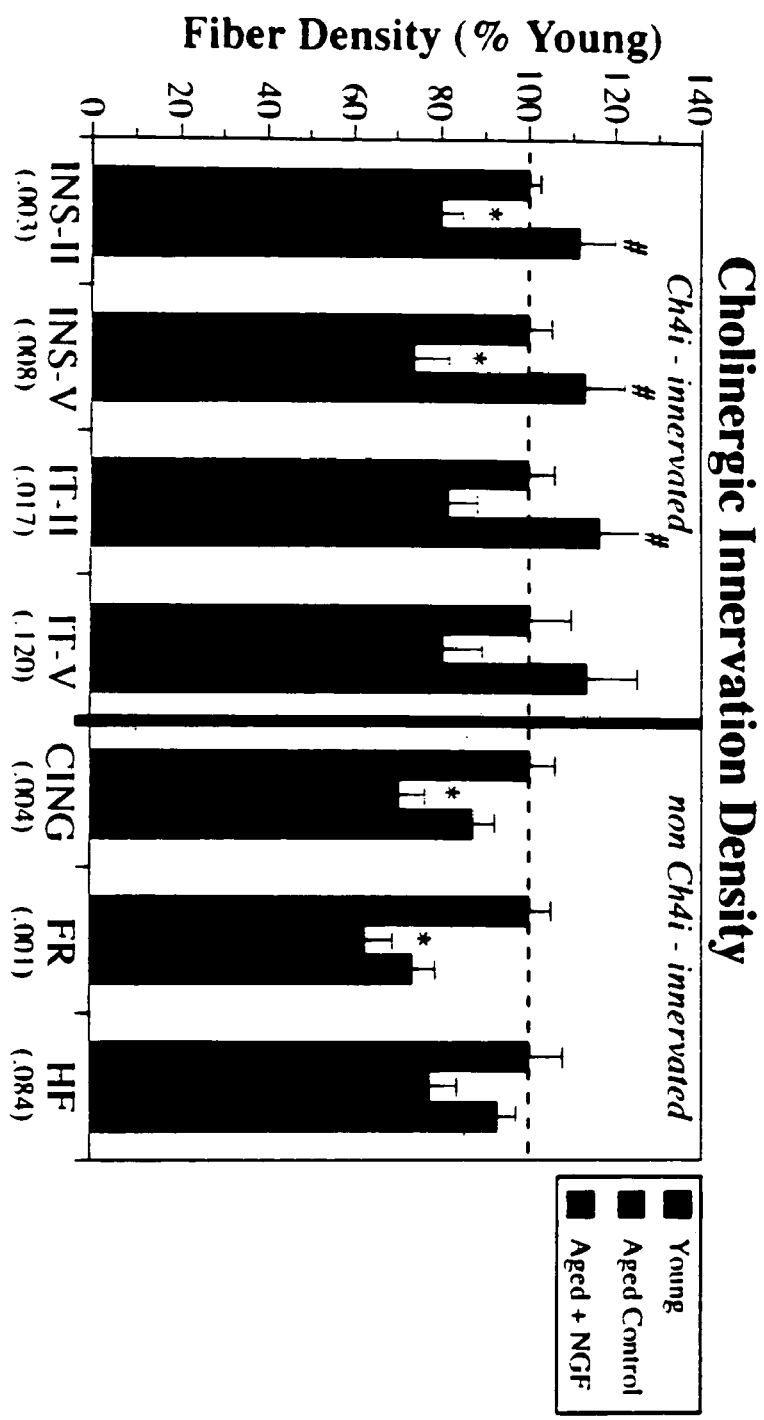
FIG. 2: Changes in Cholinergic Axon Density Across Cortical Regions.

LEGEND TO FIGS. 1–2: * —significantly reduced compared to young animals ($p<0.05$, Post hoc Fischer's);

DETAILED DESCRIPTION OF THE INVENTION

I. Primates Suffer Structural Alterations in Cholinergic Innervation of the Brain during Aging The invention provides proof, not previously established, that normal aging in the non-human primate brain is associated with a significant reduction in cholinergic innervation of the cortex, as evidenced by losses of cortical cholinergic axonal terminals. Cholinergic systems contribute only a small fraction to the total number of axons and synapses in the cortex, yet exert an important role in modulating neuronal excitability throughout the neocortex and hippocampus. Thus, alterations in this system can exert wide-ranging effects on various aspects of cognition, including attention and memory.

For example, as described in greater detail in the Examples, aged monkeys who received grafts of beta-galactosidase expressing host cells did not differ significantly from aged non-operated animals in cholinergic innervation of the various cortical fields examined. Such animals were collectively utilized as controls ("aged controls").

Aged control monkeys exhibited a significant 24.8±2.6% decline in AChE axon terminal density averaged across all cortical regions compared to non-aged subjects (p<0.0001, post-hoc Fischer's). These differences were consistent and significant across several individual cortical regions when analyzed independently, including the insular cortex, cingulate cortex and frontal cortex regions. Strong trends toward similar age-related differences in cholinergic innervation were present in inferior temporal cortex and in the hippocampal formation (id.).

II. Reversal of Age-Related Neuronal Loss in the Brain

A. Improved Cholinergic Innervation Extends from the Delivery Site

Age-related changes in cortical cholinergic innervation in diverse cortical regions were substantially reversed by cellular gene delivery of NGF. For example, aged monkeys that received grafts of NGF-secreting cells exhibited a substantial and significant reversal of age-related declines in cortical cholinergic innervation. When averaged across all cortical regions examined, NGF-grafted animals had levels of cholinergic innervation that were significantly greater than values of aged control monkeys (p<0.0001, post-hoc Fischer's) and were equal to intact young monkeys (p=0.89, post-hoc Fischer's).

Further, cortical regions (insular and inferior temporal cortices) receiving innervation primarily from the intermediate division of Ch4, the cholinergic subdivision targeted for grafting, demonstrated levels of cholinergic innervation significantly exceeding those of normal young monkeys (overall 13.4±4.5% increase relative to young monkeys; p=0.01, post-hoc Fischer's. Levels of cholinergic innervation in these regions also significantly exceeded control-aged monkeys (overall 43.6±3.0% increase; p <0.0001, post-hoc Fischer's). Cholinergic fiber densities in cortical regions (cingulate and frontal cortex, hippocampus) not heavily innervated by the targeted Ch4i cell population also exhibited reversal of age-related losses after NGF cell grafting, although the magnitude of the reversal (20.6±4.1% increase; p=0.01, post-hoc Fischer's) was more modest than that observed in temporal and insular cortex.

These effects of cellularly-delivered NGF on cortical cholinergic innervation were exerted at a distance, since the growth factor was presented to the cholinergic soma yet influenced terminal axon density in the distant cortex. Remarkably, reversal of age-related axonal attenuation in both the soma and the cortex was achieved after only three months of NGF delivery to the primate brain soma. Thus, practice of the invention significantly and efficiently ameliorates neuronal loss accompanying the normal aging process in the primate brain.

From a clinical perspective, a significant advantage provided by the invention is the ability to introduce exogenous growth factor to discrete regions of identified neuronal loss (to induce local chemotropic sprouting of axons into growth factor-secreting grafts, as shown in), while at the same time inducing a significant increase in the number or complexity of neuronal terminals via non-chemotropic influence by the growth factors in regions of the brain distant from the delivery sites. While not limiting of the scope of the invention, it can be surmised from these results that the mechanism through which growth factors influence axonal morphology at a distance may involve activation of diverse intracellular downstream signaling pathways, including PI-3 kinase and ras/erk, leading to increases in cellular transport of growth-related proteins.

B. Growth Factor Delivery: Site Selection and Dosing

To use both the local chemotropic and distant non-chemotropic effects of growth factors delivered according to the invention to advantage, specific delivery sites are preferably selected so as to cluster in an area of neuronal atrophy or loss, or likely neuronal atrophy or loss (such regions may include, but are not limited to, the cholinergic basal forebrain in normal aging, the entorhinal cortex in normal aging, and any cortical region in normal aging; the cholinergic basal forebrain or entorhinal cortex in patients with a significant history of Alzheimer's Disease, the substantia nigra in patients with Parkinson's disease, or motor neurons in patients with amyotrophic lateral sclerosis). Once areas of neuronal loss (or likely neuronal loss) are identified, delivery sites are selected for stereotaxic distribution so each unit dosage of growth factor composition is delivered into the brain at the target site, or within diffusion reach of a chemotropic (concentration) gradient leading to the target site (generally, within 500 μm of a targeted neuron).

The terms "unit dosage" and "dosage" refer to concentration of growth factor or similarly-encoding transgene delivered via recombinant expression vector or donor cell in a pharmaceutically acceptable composition ("growth factor delivery composition"). One of ordinary skill in the art will be able to adjust dosage as appropriate to the patient and his or her condition. However, depending on whether the growth factor expressing transgene is introduced by an in vivo approach (via a viral or non-viral expression vector), or by an ex vivo approach (via grafting of transgene expressing host cells to target tissue), the preferred dosing parameters vary.

For ex vivo delivery, a unit dosage of growth factor delivery composition contains a concentration of donor cells of at least $1 \times 10^5$ cells/μl. Each graft made at a delivery site is comprised of between 2 and 20 μl of a donor cell composition.

For in vivo delivery, a unit dosage of growth factor delivery composition consists of 2.5 to 10 μl of such composition, wherein the composition provides from $10^{10}$ up to $10^{12}$ growth factor expressing viral particles per ml.

Each unit dosage of growth factor delivery composition is preferably delivered to each grafting site in the target tissue through a surgical incision over a period of about 5–10 minutes (depending on the total volume of cell suspension to be delivered). The rate of delivery of the cells may therefore vary from about 0.2 μl cell suspension/minute to about 4 μl cell suspension/minute.

III. Materials for Use in Practicing the Invention

Materials useful in the methods of the invention include donor cells, recombinant expression vectors, packaging cell lines, helper cell lines, synthetic in vivo gene therapy vectors, regulatable gene expression systems, encapsulation materials, pharmaceutically acceptable carriers and polynucleotides coding for growth factors of interest.

A. Nervous System Growth Factors

Known nervous system growth factors include nerve growth factor (NGF), brain-derived neurotrophic factor (BDNF), neurotrophin-3 (NT-3), neurotrophin-4/5 (NT-4/5), neurotrophin-6 (NT-6), ciliary neurotrophic factor (CNTF), glial cell line-derived neurotrophic factor (GDNF), the fibroblast growth factor family (FGF's 1–15), leukemia inhibitory factor (LIF), certain members of the insulin-like growth factor family (e.g., IGF-1), the neurturins, persephin, the bone morphogenic proteins (BMPs), the immunophilins, the transforming growth factor (TGF) family of growth factors, the neuregulins, epidermal growth factor (EGF), platelet-derived growth factor (PDGF), and others. NGF and NT-3 in particular have been tested with promising results in clinical trials and animal studies (see, e.g., Hefti and Weiner, Ann Neurol., 20:275–281 (1986); Tuszynki and Gage, Ann. Neurol., 30:625–636 (1991); Tuszynski, et al., Gene Therapy, 3:305–314 (1996) and Blesch and Tuszynski, Clin.Neurosci., 3:268–274 (1996)). Of the known nervous system growth factors, human NGF ,BDNF, NT-3 and GDNF are preferred for use in the invention for their relatively low immunogenicity as compared to allogenic growth factors.

Coding polynucleotides for hNGF ,BDNF, NT-3 and GDNF are known, as are coding sequences for growth factors of other mammalian species (e.g., mouse, in which the coding sequence for NGF is highly homologous to the human coding sequence). For example, a cDNA including the coding sequence for hNGF is reported in GenBank at E03015 (Kazuo, et al., Japanese Patent Application No. JP19911175976-A, while the nucleotide sequence of genomic hNGF (with putative amino acid sequence) is reported in GenBank at HSBNGF (Ullrich, Nature, 303: 821–825 (1983)) and the mRNA sequence is reported in GenBank at Accession No. X52599; locus HSBNGFAC (Borsani, et al., Nucleic Acids Res., 18:4020 (1990)). The genomic nucleotide sequence of hNT3 is reported in GenBank at E07844 (Asae, et al., JP Patent Application No. 1993189770-A4). These references are incorporated herein to illustrate knowledge in the art concerning nucleotide and amino acid sequences for use in synthesis of growth factor.

B. In Vivo And Ex Vivo Recombinant Expression Vectors

1. Identity.

The strategy for preparing genes for transfer into target cells in the brain includes the following basic steps: (1) selection of an appropriate growth factor expressing transgene; (2) selection and development of suitable and efficient vectors for gene transfer; (3) in vivo transduction of target cells, or grafting of donor cells to target tissue; (4) demonstration that transgene expression occurs stably and efficiently; (5) demonstration that the delivery procedure caused no serious deleterious effects; and (6) demonstration of a desired phenotypic effect in the host animal.

For either in vivo or ex vivo delivery, because adult mammalian brain cells are non-dividing, the recombinant expression vector chosen must be able to transduce and be expressed in non-dividing cells. At present, vectors known to have this capability include DNA viruses such as adenoviruses and certain RNA viruses such as HIV-based lentiviruses and feline immunodeficiency virus (FIV). Other vectors with this capability include herpes simplex virus (HSV). A HIV-based lentiviral vector has recently been developed which, like other retroviruses, can insert a transgene into the nucleus of host cells (enhancing the stability of expression) but, unlike other retroviruses, can make the insertion into the nucleus of non-dividing cells. This lentiviral vector has been shown to stably transduce brain cells after direct injection and stably express a foreign transgene without detectable pathogenesis from viral proteins (see, Naldini, et al., Science, 272:263–267 (1996), the disclosure of which is incorporated by reference). Following the teachings of the researchers who first constructed the HIV-1 retroviral vector, those of ordinary skill in the art will be able to construct lentiviral vectors suitable for use in the methods of the invention (for more general reference concerning retrovirus construction, see, e.g., Kriegler, Gene Transfer and Expression, A Laboratory Manual, W. Freeman Co. (NY 1990) and Murray, E J, ed., Methods in Molecular Biology, Vol. 7, Humana Press (NJ 1991)).

Adenoviruses and AAV have been shown to be quite safe for in vivo use and have been shown to result in long-term gene expression in vivo; they are therefore a preferred choices for use in the in vivo methods of the invention, where safety and long-term expression of growth factor encoding transgenes is necessary. Those of ordinary skill in the art are familiar with the techniques used to construct adenoviral and AAV vectors and can readily employ them to produce vector compositions useful in the claimed invention (for reference, see, e.g., Straus, The Adenovirus, Plenum Press (NY 1984), pp. 451–496; Rosenfeld, et al., Science, 252:431–434 (1991); U.S. Pat. No. 5,707,618 [adenovirus vectors for use in gene therapy]; and U.S. Pat. No. 5,637,456 [method for determining the amount of functionally active adenovirus in a vector stock], the contents of each of which is incorporated herein to illustrate the level of skill in the art).

Herpesviruses, alpha viruses and pox viruses are also well-characterized virus vectors which may be applied to the methods of the invention. Of these vectors, adeno-associated vectors are an especially attractive choice for their lack of pathogenicity and ability to insert a transgene into a host genome.

Non-viral delivery methods are also an option for use in the in vivo methods of the invention. In particular, the plasmid (in a "naked" or lipid-complexed form), lipoplexes (liposome complexed nucleic acids), amino acid polymer complexes with nucleic acids and artificial chromosomes are all non-viral gene delivery agents which are demonstrably able to transduce cells and deliver a foreign transgene. Synthetic in vivo gene therapy vectors are also an option for use in the methods of the invention.

For ex vivo use, retroviral vectors (especially those of murine origin) offer an efficient, useful, and presently the best-characterized means of introducing and expressing foreign genes efficiently in mammalian cells. These vectors have very broad host and cell type ranges, integrate by reasonably well understood mechanisms into random sites in the host genome, express genes stably and efficiently, and under most conditions do not kill or obviously damage their host cells.

2. Construction.

Construction of vectors for recombinant expression of nervous system growth factors for use in the invention may be accomplished using conventional techniques which do not require detailed explanation to one of ordinary skill in the art. For review, however, those of ordinary skill may wish to consult Maniatis et al., in Molecular Cloning: A Laboratory Manual, Cold Spring Harbor Laboratory, (NY 1982).

Briefly, construction of recombinant expression vectors employs standard ligation techniques. For analysis to confirm correct sequences in vectors constructed, the ligation mixtures may be used to transform a host cell and successful transformants selected by antibiotic resistance where appropriate. Vectors from the transformants are prepared, analyzed by restriction and/or sequenced by, for example, the method of Messing, et al., (Nucleic Acids Res., 9:309, 1981), the method of Maxam, et al., (Methods in Enzymology, 65:499, 1980), or other suitable methods which will be known to those skilled in the art. Size separation of cleaved fragments is performed using conventional gel electrophoresis as described, for example, by Maniatis, et al., (Molecular Cloning, pp. 133–134, 1982).

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Banerji et al., Cell 27:299 (1981); Corden et al., Science 209:1406 (1980); and Breathnach and Chambon, Ann. Rev. Biochem. 50:349 (1981)). For retroviruses, control elements involved in the replication of the retroviral genome reside in the long terminal repeat (LTR) (Weiss et al., eds., The molecular biology of tumor viruses: RNA tumor viruses, Cold Spring Harbor Laboratory, (NY 1982)). Moloney murine leukemia virus (MLV) and Rous sarcoma virus (RSV) LTRs contain promoter and enhancer sequences (Jolly et al., Nucleic Acids Res. 11:1855 (1983); Capecchi et al., In: Enhancer and eukaryotic gene expression, Gulzman and Shenk, eds., pp. 101–102, Cold Spring Harbor Laboratories (NY 1991). Other potent promoters include those derived from cytomegalovirus (CMV) and other wild-type viral promoters.

Promoter and enhancer regions of a number of non-viral promoters have also been described (Schmidt et al., Nature 314:285 (1985); Rossi and de Crombrugghe, Proc. Natl. Acad. Sci. USA 84:5590–5594 (1987)). Methods for maintaining and increasing expression of transgenes in quiescent cells include the use of promoters including collagen type I (1 and 2) (Prockop and Kivirikko, N. Eng. J. Med. 311:376 (1984); Smith and Niles, Biochem. 19:1820 (1980); de Wet et al., J. Biol. Chem., 258:14385 (1983)), SV40 and LTR promoters.

In addition to using viral and non-viral promoters to drive transgene expression, an enhancer sequence may be used to increase the level of transgene expression. Enhancers can increase the transcriptional activity not only of their native gene but also of some foreign genes (Armelor, Proc. Natl. Acad. Sci. USA 70:2702 (1973)). For example, in the present invention collagen enhancer sequences are used with the collagen promoter 2(I) to increase transgene expression. In addition, the enhancer element found in SV40 viruses may be used to increase transgene expression. This enhancer sequence consists of a 72 base pair repeat as described by Gruss et al., Proc. Natl. Acad. Sci. USA 78: 943 (1981); Benoist and Chambon, Nature 290:304 (1981), and Fromm and Berg, J. Mol. Appl. Genetics, 1:457 (1982), all of which are incorporated by reference herein. This repeat sequence can increase the transcription of many different viral and cellular genes when it is present in series with various promoters (Moreau et al., Nucleic Acids Res. 9:6047 (1981).

Transgene expression may also be increased for long term stable expression using cytokines to modulate promoter activity. Several cytokines have been reported to modulate the expression of transgene from collagen 2(I) and LTR promoters (Chua et al., connective Tissue Res., 25:161–170 (1990); Elias et al., Annals N.Y. Acad. Sci., 580:233–244 (1990)); Seliger et al., J. Immunol. 141:2138–2144 (1988) and Seliger et al., J. Virology 62:619–621 (1988)). For example, transforming growth factor (TGF), interleukin (IL)-1, and interferon (INF) down regulate the expression of transgenes driven by various promoters such as LTR. Tumor necrosis factor (TNF) and TGF1 up regulate, and may be used to control, expression of transgenes driven by a promoter. Other cytokines that may prove useful include basic fibroblast growth factor (bFGF) and epidermal growth factor (EGF).

Collagen promoter with the collagen enhancer sequence (Coll(E)) can also be used to increase transgene expression by suppressing further any immune response to the vector which may be generated in a treated brain notwithstanding its immune-protected status. In addition, anti-inflammatory agents including steroids, for example dexamethasone, may be administered to the treated host immediately after vector composition delivery and continued, preferably, until any cytokine-mediated inflammatory response subsides. An immunosuppression agent such as cyclosporin may also be administered to reduce the production of interferons, which downregulates LTR promoter and Coll(E) promoter-enhancer, and reduces transgene expression.

It is also useful to be able to regulate the secretion of the genetically engineered gene product after grafting. The release of a gene product such as acetylcholine (ACh), a transmitter that is greatly decreased through degeneration of cholinergic neuron populations, from cultured cells infected with a MLV vector expressing the choline acetyltransferase cDNA can be augmented using choline, a precursor for acetylcholine. This suggests a means for dietary regulation of intracerebral gene therapy.

C. Pharmaceutical Preparations of Gene Vectors

Growth factor delivery compositions may consist of expression vectors or donor cells placed into a pharmaceutically acceptable suspension, solution or emulsion. Suitable mediums include saline and may, for those embodiments which do not rely on antigen presenting cells for delivery of the growth factor transgenes into target tissue, liposomal preparations.

More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Further, a composition of growth factor transgenes may be lyophilized using means well known in the art, for subsequent reconstitution and use according to the invention.

A colloidal dispersion system may also be used for targeted gene delivery. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome.

IV. Methods for Delivery of Transgene Delivery Composition

The most effective mode and timing of injection of the growth factor delivery compositions of the invention will vary with the patient's health, response to treatment, and the judgment of the treating health professional.

Direct delivery of the growth factor delivery compositions of the invention may be achieved by means familiar to those of skill in the art, including microinjection (see, e.g., Capecchi, Cell, 22:479–488 (1980); electropotation (see, e.g., Andreason and Evans, Biotechniques, 6:650–660 (1988);

infusion, chemical complexation with a targeting molecule or co-precipitant (e.g., liposome, calcium), and microparticle bombardment (Tang, et al., Nature, 356:152–154 (1992)).

V. Animal Models and Clinical Evaluation

Data demonstrating the use and efficacy of the methods of the invention in an aged, non-human primate model (used to best approximate the size requirements of the primate brain) are provided in the Examples.

Clinical evaluation and monitoring of treatment can be performed using the in vivo imaging techniques described above as well as through biopsy and histological analysis of treated tissue. In the latter respect, basal forebrain cholinergic neuronal numbers can be quantified in a tissue sample using, for example, anti-growth factor antibody (for immunoassay of secreted growth factor) or NGF-receptor (p75) and choline acetyltransferase (ChAT) for labeling of neurons. A sample protocol for in vitro histological analysis of treated and control tissue samples is described in the Examples.

The invention having been fully described, examples illustrating its practice are set forth below. These examples should not, however, be considered to limit the scope of the invention, which is defined by the appended claims. Those of ordinary skill in the art will appreciate that while the Examples illustrate an ex vivo application of the invention, the results achieved will be accessible through in vivo delivery of the nervous system growth factor encoding transgenes described, as taught herein, with in vivo gene delivery sites and direct delivery means substituted for the grafting sites and grafting methods discussed in the Examples.

In the examples, the abbreviation "min." refers to minutes, "hrs" and "h" refer to hours, and measurement units (such as "ml") are referred to by standard abbreviations. All printed materials cited are incorporated herein by reference.

EXAMPLE I

Primate Animal Model of Loss of Cholinergic Neuronal Function

Twelve aged and four adult non-aged Macaca mulatta (rhesus) monkeys were experimental subjects. Non-aged animals (n=4, mean age=9.64±1.90 yrs) did not undergo surgical procedures and their intact brains were studied. Aged monkeys were divided into two experimental groups: NGF recipients (n=6, mean age=22.55±0.56 yrs) and control subjects (n=6, mean age=23.51±1.07 yrs). All procedures and animal care adhered strictly to NIH, AAALAC, USDA, Society for Neuroscience, and internal institutional guidelines for experimental animal health, safety and comfort.

EXAMPLE II

Preparation of h-NGF Secreting Fibroblasts

For NGF delivery to aged subjects, monkeys received intraparenchymal grafts of autologous fibroblasts genetically modified to produce and secrete human NGF, as previously described. Briefly, autologous fibroblasts obtained from skin biopsies were genetically modified in vitro to produce and secrete the active portion of human NGF. Transduction procedures were carried out using replication-incompetent retroviral vectors derived from Moloney murine leukemia virus (MLV). Transduced cells were selected by growth in the neomycin analog G418. Production of biologically active NGF was verified by induction of neurite outgrowth from PC12 cells as described; production of NGF mRNA was determined by Northern blot; and amounts of NGF produced from cells were assayed by NGF ELISA specific for human NGF and sensitive to 5 pg/ml. Optimal NGF-producing bulk clones were amplified to numbers sufficient for in vivo grafting by serial passaging. Cells were harvested by gentle trypsinization for in vivo grafting.

EXAMPLE III

Intraparenchymal Delivery of Fibroblasts Genetically Modified to Produce h-NGF

Monkeys underwent pre-operative MRI scans (see, Tuszynski, et al., Gene Therapy, 3:305–314, 1996) to visualize basal forebrain target grafting regions (see, Mesulam et al., J.Comp.Neurol., 214:170–197, 1983). After generating stereotaxic grafting coordinates from MRI scans, each monkey received intraparenchymal grafts of autologous NGF-secreting fibroblasts.

Stereotactic coordinates for surgery were generated from magnetic resonance images (MR) of the brain of each subject. The rostral and caudal boundaries of Ch4 were identified on each subject's MR scan, making reference to primate histological brain sections and to standard primate brain atlases. The total rostral-caudal distance of Ch4 was measured on the MR scan, and five graft injection sites were chosen that were equally distributed over this rostral-caudal distance.

The sites for desired ventral-dorsal (VD) and medial-lateral (ML) injections were chosen such that cell grafts were deposited just dorsal to the desired target at each coordinate (within 500 um), and exactly centered in the mediolateral (ML) plane at the maximal density of cholinergic neuronal somata (estimated by review of histological sections at the corresponding AP level). Thus, five grafts were deposited on each side of the Ch4 region per subject, or ten total grafts per subject. Real-time coordinates for in vivo injections were calculated from calibration scales on the MR image. Subjects underwent surgical grafting in the same stereotaxic apparatus that MR scans were performed in.

To place the grafts, animals were placed into a primate stereotaxic apparatus and a midline scalp incision was used to expose the skull. The AP and ML stereotaxic coordinates for the BFC system were used to define the margins of the craniotomy site. Following craniotomy, a ML zero reference point was obtained by measuring the midpoint of the superior sagittal sinus. The dura was incised and reflected to expose the pial surface. The pial surface at each injection site was used as a VD zero reference point for that injection site.

Using the zero reference points obtained in the AP, ML, and VD planes and the stereotaxic injection coordinates calculated from that animal's MR scan, 5 ul of cells were injected into each of 5 sites over the rostral-caudal extent of the Ch4 targeted region bilaterally (10 grafts total per animal) using 25-gauge Hamilton syringe. Grafts were generally targeted to a position slightly dorsal to but within 500 um of Ch4 nuclei. The injection rate was controlled at 5 ul/min. Cells were injected at a concentration of $1.0 \times 10^5$ cells/ul (for a total of 10 million grafted cells per animal), a concentration that optimally maintains cells in suspension without clumping but sufficiently concentrated to maximize number of surviving cells in vivo. Monkeys survived for three months before sacrifice.

Some control aged subjects received intraparenchymal grafts as noted above. These grafted cells consisted either of autologous fibroblasts transduced to express the reporter gene beta-galactosidase (n=6 monkeys). Beta-gal production was assessed in vitro using a specific anti-beta-gal antibody. Cells were grafted into intraparenchymal sites in numbers identical to those described above for NGF graft recipients.

For all surgical procedures, primates were preanesthetized with 25 mg/kg ketamine IM. They were then anesthetized with isoflurane administered by endotracheal intubation. Post-operatively animals were closely monitored, and received supportive care and appropriate analgesics when indicated. Animals were placed in the same primate stereotaxic apparatus (Crist Instruments) that was used to perform MRI scans. A midline scalp incision exposed the skull. A 2.5×5 cm sagittally oriented craniotomy was performed on each side of the hemicranium, and the dura was incised and reflected to expose sites for stereotaxically guided cell injections. Ten ul of cells were injected into each site through a 25 ga. Hamilton syringe at a rate of 1 ul/minute. Postoperatively, all experimental subjects were observed closely for signs of discomfort or toxicity. After a three-month survival period, animals were perfused transcardially for one hour with a 4% solution of paraformaldehyde in 0.1M phosphate buffer followed by 5% sucrose solution in the same buffer for 20 minutes. The brain was stereotaxically blocked in the coronal plane.

EXAMPLE IV

Quantification of Cholinergic Innervation Density

An intersect analysis was used to obtain a quantitative estimate of cholinergic axon density in several different cortical regions described below, using standardized methods developed by Geula and Mesulam (Geula, C., and Mesulam, M. M. (1996), Cerebral Cortex 6, 165–77).

Briefly, very high resolution digital images of AChE-stained, 40 um-thick sections were captured from an Olympus AX-70 microscope at 360× magnification (600× for hippocampus) with high numerical aperture optics using a digital Spot camera (Diagnostics Instruments Inc., Sterling Heights, Mich.) with a computer interface. Images were displayed on a high-resolution Sony monitor, and a 6×6 grid (175 μm×175 μm for 360×) was superimposed on each quantification frame using Adobe Photoshop.

The number of AChE-stained axons intersecting all gridlines in the field were quantified and summed in each image. Two fields per animal were quantified in this manner from each of the following cortical regions (nomenclature of Paxinos et al. (Paxinos, G., Huang, X.-F., and Toga, A. W. (2000). The Rhesus Monkey Brain in Stereotaxic Coordinates (San Diego: Academic Press): inferior temporal cortex layers II (IT-II) and V (IT-V), insular cortex layers II (INS-II) and V (INS-V), cingulate cortex layer II (CING), frontal cortex layer II (FR), and hippocampal formation (HF; stratum radiatum of CA1). Fields were sampled bilaterally from every animal in each region. This method of analysis was chosen because it is capable of quantifying cholinergic fiber numbers, independent of the intensity of the AChE staining intensity (Geula and Mesulam, supra, 1996). Multiple group comparisons were made by analysis of variance (ANOVA) with post-hoc analysis using Fisher's least square difference. Biological significance was established at the 95% confidence level. Data are presented as mean±standard error of the mean.

Aged β-gal-grafted animals did not differ significantly from aged non-operated animals in cholinergic innervation of the various cortical fields examined in this study and were therefore combined into a single group ("aged controls"). When averaged across all cortical regions, overall group differences in cholinergic axon innervation density were present (p<0.0001, ANOVA). Aged control monkeys exhibited a significant 24.8±2.6% decline in AChE axon terminal density averaged across all cortical regions compared to non-aged subjects (p<0.0001, post-hoc Fischer's). These differences were consistent and significant across several individual cortical regions when analyzed independently, including insular cortex, cingulate cortex and frontal cortex. Strong trends toward similar age-related differences in cholinergic innervation were present in inferior temporal cortex and in the hippocampal formation.

EXAMPLE V

Cellelar NGF Delivery Reverses Age-Related Reductions in Cholinergic Innervation Aged monkeys that received grafts of NGF-secreting cells exhibited a substantial and significant reversal of age-related declines in cortical cholinergic innervation. When averaged across all cortical regions examined in this study, NGF-grafted animals had levels of cholinergic innervation that were significantly greater than values of aged control monkeys (p<0.0001, post-hoc Fischer's) and were equal to intact young monkeys (p=0.89, post-hoc Fischer's). Further, cortical regions (insular and inferior temporal cortices) receiving innervation primarily from the intermediate division of Ch4, the cholinergic subdivision targeted for grafting, demonstrated levels of cholinergic innervation significantly exceeding those of normal young monkeys (overall 13.4±4.5% increase relative to young monkeys; p=0.01, post-hoc Fischer's).

Levels of cholinergic innervation in these regions also significantly exceeded control-aged monkeys (overall 43.6±3.0% increase; p<0.0001, post-hoc Fischer's). Cholinergic fiber densities in cortical regions (cingulate and frontal cortex, hippocampus) not heavily innervated by the targeted Ch4i cell population also exhibited reversal of age-related losses after NGF cell grafting, although the magnitude of the reversal (20.6±4.1% increase; p=0.01, post-hoc Fischer's) was more modest than that observed in temporal and insular cortex. These effects of cellularly-delivered NGF on cortical cholinergic innervation were exerted at-a-distance, since the growth factor was presented to the cholinergic soma yet influenced terminal axon density in the distant cortex.

To determine whether NGF delivery simply increased AChE expression in neurons, thereby enhancing the intensity of the AChE stain without actually altering the density of axons, an additional analysis was performed. Sections from young intact, NGF-grafted, and β-gal grafted monkeys were blindly rated by two independent observers for intensity (darkness) of the AChE stain, examining those regions specifically used in the quantitative analysis. Using a rank scale of 0–5 (0=lightly stained, 5=very darkly stained), the mean overall intensity/darkness of the AChE staining did not differ significantly between groups of animals (p=0.3, ANOVA) nor between the blinded observers. Thus, findings of this study are not a result of enhanced AChE staining in the NGF grafted group, and represent actual differences in the number of axonal processes.

In short, cellular delivery of growth factor according to the invention ameliorates cholinergic neuronal atrophy and loss in the normal aging brain. Further, this result is achieved without the adverse effects of infused growth factor therapy that have been previously observed, such as weight loss, Schwann cell migration/proliferation, and sprouting of sensory or sympathetic axons (either in the immediate treatment area or in other regions of the brain). Advantageously, growth factor production from cell grafts placed as described persisted for at least eight months in vivo in the primate brain, as determined by fresh dissection of grafts and determination of growth factor protein levels by ELISA (25 ng/mg tissue). Indeed, transgene expression from these cells can persist for as long as 18 months (based on results achieved in the rodent central nervous system).

EXAMPLE VI

Histology Confirming in Vivo Uptake of Donor Cells Expression of NGF and Lack of Beta-Amyloid Induction Sections of brain tissue after humane sacrifice of the test animals were cut at 40 um intervals on a freezing microtome. Every sixth section was processed for Nissl stain or hematoxylin and eosin. Immunocytochemical labeling against -amyloid was performed using an amyloid-specific monoclonal antibody (anti-A4). Sections lacking primary antibody were processed to verify specificity of labeling. A representative section per subject was quantified from each of the following regions: temporal, frontal, cingulate, insular, parietal and occipital cortices; amygdala and hippocampus; and the intermediate division of the Ch4 region (Nucleus Basalis of Meynert). Sampled sections from each subject were closely matched in region and size. The total number of amyloid plaques per region was quantified and recorded. Observers were blinded to the identity of the tissue being quantified.

All grafted subjects showed surviving cell grafts within 500 um of each grafting site. There was no qualitative difference in fibroblast morphology and overall graft size between NGF- and control-graft recipients. Grafts were most frequently located adjacent to the intermediate division of the Ch4 region of the basal forebrain, but in all cases included at least one graft located within the anterior and posterior divisions of the Ch4 region.

No amyloid plaques at all were detected in adult, non-aged primate tissue. In contrast, control aged monkeys showed a significant increase in amyloid immunolabeling in the frontal, temporal insular and cingulate cortices and amygdala, and extremely small increases in the parietal cortex and hippocampus relative to non-aged monkeys. No plaques at all were present in the cholinergic basal forebrain in any group.

In aged control animals, plaques typically showed a dense central core and a less dense surrounding halo of immunreactive deposition product, an appearance typical of "mature" plaques observed in AD. This immunolabeling pattern is consistent with previous reports in aged primate brain. However, no increase in amyloid labeling was observed in the aged, NGF-grafted brains, indicating that three months of intraparenchymal NGF delivery does not increase beta-amyloid plaque deposition in the aged primate brain. Thus, the benefits of NGF grafting in the brains of primates exhibiting AD symptoms can be achieved without risk of stimulating amyloid deposition in response to the graft trauma.

Initially, group differences were statistically determined by analysis of variance, with post-hoc analysis utilizing Fisher's least square difference. However, since non-aged adult monkeys showed no amyloid plaques, comparisons between NGF-treated and control aged monkeys were made using unpaired two-way student's t-test.

What is claimed is:

1. A method for ameliorating neuronal atrophy and loss in the mammalian brain, the method comprising directly delivering a neurotrophin-encoding transgene composition comprising a recombinant expression vector containing said neurotrophin-encoding trnasgene to preselected delivery sites in the brain for expression of the neurotrophin at, or within diffusion distance of, targeted cholinergic or dopaminergic neurons, wherein the neurotrophin is nerve growth factor (NGF) or glial derived nerve growth factor (GDNF) and stimulates non-chemotrophic axonal growth by, or activity in, the targeted neurons.

2. The method according to claim 1, wherein the targeted neurons are cholinergic neurons.

3. The method according to claim 2, wherein the stimulation occurs in a cortical region of the brain innervated by the targeted cholinergic neurons.

4. The method according to claim 3, wherein each delivery site is preselected by correlating sites of potential loss of cortical fiber density to potential impairment of neurological function in the brain.

5. The method according to claim 4, wherein the cortical region of the brain is the insular or temporal cortex.

6. The method according to claim 3, wherein the stimulation occurs in the cingulate, frontal, entorhinal or hippocampal cortices.

7. The method according to claim 2, wherein the stimulation occurs in the cholinergic forebrain.

8. The method according to claim 3 or 7, wherein the region of the brain containing the targeted neurons is the striatum.

9. The method according to claim 7, wherein the treated mammal is a human with Alzheimer's Disease.

10. The method according to claim 1, wherein the targeted neurons are dopaminergic neurons.

11. The method according to claim 10, wherein the stimulation occurs in dopaminergic neurons innervating the substantia nigra.

12. The method according to claim 11, wherein the region of the brain containing the targeted dopaminergic neurons is the striatum.

13. The method according to claim 10, wherein the treated mammal is a human with Parkinson's Disease.

14. The method according to claim 1, wherein the transgene-expressing recombinant expression vector is a viral vector.

15. The method according to claim 14, wherein the viral vector is delivered in a pharmaceutically acceptable composition, and provides from $10^{10}$ to $10^{12}$ viral particles/ml of composition.

16. The method according to claim 14, wherein the viral vector is an adeno-associated viral vector.

17. The method according to claim 14, wherein the viral vector is a lentivixal vector.

18. The method according to claim 1, wherein the mammal is a human and the transgene encodes a human NGF or GDNF molecule.

19. The method according to claim 18, wherein the transgene encodes human NGF.

20. The method according to claim 18, wherein the transgene encodes human GDNF.

21. The method according to claim 1, wherein the mammal is a human with aging-related impairment.

* * * * *